US012644878B2

(12) United States Patent
Saxena et al.

(10) Patent No.: US 12,644,878 B2
(45) Date of Patent: Jun. 2, 2026

(54) METHOD FOR ESTIMATING HYDROCARBON SATURATION OF A ROCK

(71) Applicant: SHELL OIL COMPANY, Houston, TX (US)

(72) Inventors: Nishank Saxena, Houston, TX (US); Amie Marie Hows, Houston, TX (US); Matthias Appel, Houston, TX (US); John Justin Freeman, Houston, TX (US)

(73) Assignee: SHELL USA, INC.

( * ) Notice: Subject to any disclaimer, the term of this patent is extended or adjusted under 35 U.S.C. 154(b) by 706 days.

(21) Appl. No.: 17/775,720

(22) PCT Filed: Dec. 10, 2020

(86) PCT No.: PCT/US2020/064180
§ 371 (c)(1),
(2) Date: May 10, 2022

(87) PCT Pub. No.: WO2021/119235
PCT Pub. Date: Jun. 17, 2021

(65) Prior Publication Data
US 2022/0404330 A1      Dec. 22, 2022

Related U.S. Application Data

(60) Provisional application No. 62/947,091, filed on Dec. 12, 2019.

(51) Int. Cl.
*G01V 3/38* (2006.01)
*E21B 49/00* (2006.01)
(Continued)

(52) U.S. Cl.
CPC ......... *G01N 33/241* (2013.01); *G01N 15/088* (2013.01); *G06T 7/0004* (2013.01); *G01N 2015/0846* (2013.01); *G06T 2200/04* (2013.01)

(58) Field of Classification Search
CPC .............. G01N 33/241; G01N 15/088; G01N 2015/0846; G01N 2223/616;
(Continued)

(56) References Cited

U.S. PATENT DOCUMENTS 8,219,319 B2    7/2012  Skelt
8,311,788 B2    11/2012  Hurley et al.
(Continued)

FOREIGN PATENT DOCUMENTS

WO      WO-2011075280 A2 *  6/2011    .............. G01V 9/00
WO      2014142976 A1    9/2014

OTHER PUBLICATIONS

Saxena, Rock properties from micro-CT images: Digital rock transforms for resolution, pore volume, and field of view, Advances in Water Resources 134 (2019) 103419 (Year: 2019).*
(Continued)

*Primary Examiner* — Vu Le
*Assistant Examiner* — Lei Zhao
(74) *Attorney, Agent, or Firm* — SHELL USA, INC.

(57) ABSTRACT

The present invention provides a method for estimating hydrocarbon saturation of a hydrocarbon-bearing rock from a resistivity log and a rock image. The image is segmented to represent either a pore space or solid material in the rock. An image porosity is estimated from the segmented image, and a corrected porosity is determined to account for the sub-resolution porosity missing in the image of the rock. A corrected cementation exponent of the rock is determined from the image porosity and the corrected porosity and is used to estimate the hydrocarbon saturation. A backpropagation-enabled trained model can be used to segment the image. A backpropagation-enabled method can be used to estimate the hydrocarbon saturation using an image selected
(Continued)

from a series of 2D projection images, 3D reconstructed images and combinations thereof.

8 Claims, 2 Drawing Sheets

(51) Int. Cl.

| | |
|---|---|
| *G01N 15/08* | (2006.01) |
| *G01N 23/046* | (2018.01) |
| *G01N 33/24* | (2006.01) |
| *G01V 11/00* | (2006.01) |
| *G06T 7/00* | (2017.01) |
| *G06T 7/11* | (2017.01) |
| *G06T 7/136* | (2017.01) |
| *G06T 7/62* | (2017.01) |

(58) Field of Classification Search
CPC ............ G01N 2223/649; G01N 23/046; G06T 7/0004; G06T 2200/04; G06T 7/62; G06T 2207/10081; G06T 2207/20081; G06T 2207/20084; G06T 7/11; G06T 7/136; G01V 3/38; G01V 11/00; E21B 49/00
See application file for complete search history.

(56) References Cited

U.S. PATENT DOCUMENTS

| | | | |
|---|---|---|---|
| 9,070,049 | B2 | 6/2015 | Fredrich et al. |
| 9,134,457 | B2 | 9/2015 | Hurley et al. |
| 10,466,386 | B2 | 11/2019 | Hurley |
| 2011/0066404 | A1 | 3/2011 | Salazar-Tio et al. |
| 2012/0275658 | A1 | 11/2012 | Hurley et al. |
| 2013/0018641 | A1 | 1/2013 | Prisco et al. |
| 2014/0044315 | A1 | 2/2014 | Derzhi et al. |
| 2015/0043787 | A1 | 2/2015 | Fredrich et al. |
| 2018/0121579 | A1 | 5/2018 | Fredrich et al. |
| 2018/0321127 | A1 | 11/2018 | León Carrera et al. |

OTHER PUBLICATIONS

Archie, The Electrical Resistivity Log as an Aid in Determining Some Reservoir Characteristics, Transactions of the AIME, 1942 (Year: 1942).*

Etnyre, Finding Oil and Gas From Well Logs, Springer Science+ Business Media New York, 1989 (Year: 1989).*

Sudakov, Driving Digital Rock towards Machine Learning: predicting permeability with Gradient Boosting and Deep Neural Networks, arXiv:1803.00758v2 [physics.geo-ph] Mar. 14, 2018 (Year: 2018).*

Office Action Received for Chinese Application No. 202080082651. 3, Mailed on Apr. 24, 2024, 17 Pages(09 Pages of English Translation and 07 Pages of Official Copy).

International Search Report and Written Opinion received for PCT Patent Application No. PCT/US2020/064180, Mailed on Mar. 16, 2021, 11 Pages.

Saxena et al., "Rock Properties From Micro-CT Images: Digital Rock Transforms for Resolution, Pore Volume, and Field of View", Advances in Water Resources, vol. 134, Sep. 10, 2019, 13 Pages, XP085905530.

Saxena et al., "Estimating Pore Volume of Rocks From Pore-Scale Imaging", Transport in Porous Media, vol. 129, Issue No. 1, May 11, 2019, pp. 403-412, XP036832637.

Garba et al., "Electrical Formation Factor of Clean Sand From Laboratory Measurements and Digital Rock Physics", Solid Earth Discuss, vol. 10, Issue No. 5, Jan. 1, 2019, pp. 1505-1517, XP055781308.

Lin et al., "Quantification of Sub-resolution Porosity in Carbonate Rocks by Applying High-salinity Contrast Brine Using X-ray Microtomography Differential Imaging", Advances in Water Resources, vol. 96, Aug. 3, 2016, pp. 306-322, XP029723812.

Saxena et al., "Estimating Electrical Cementation and Saturation Exponents Using Digital Rock Physics", Journal of Petroleum Science and Engineering, vol. 198, Dec. 3, 2020, XP086434571.

Archie, "Classification of Carbonate Reservoir Rocks and Petrophysical Considerations", Bulletin of the American Association of Petroleum Geologists, vol. 36, Issue No. 2, Feb. 1, 1952, pp. 278-298.

Archie, "The Electrical Resistivity Log as an Aid in Determining Some Reservoir Characteristics ", Transactions of the AIME, vol. 146, Issue No. 1, Dec. 1942, pp. 54-62.

Otsu, "A Threshold Selection Method From Gray-level Histogram", IEEE Transactions on Systems, Man, and Cybernetics, vol. 9, Issue No. 1, Jan. 1979, pp. 62-66.

Andra et al., "Digital Rock Physics Benchmarks—Part II: Computing Effective Properties", Computers and Geosciences, vol. 50, Jan. 2013, pp. 33-43.

Saxena et al., "Effect of Image Segmentation & Voxel Size on Micro-CT Computed Effective Transport & Elastic Properties", Marine and Petroleum Geology, vol. 86, Sep. 1, 2017, pp. 972-990.

Chuang et al., "Fuzzy C-means Clustering With Spatial Information for Image Segmentation", Computerized Medical Imaging and Graphics, vol. 30, Issue No. 1, Feb. 2006, pp. 9-15.

Garboczi, "Finite Element and Finite Difference Programs for Computing the Linear Electric and Elastic Properties of Digital Images of Random Materials", NISTIR 6269, Dec. 1, 1998, 213 Pages.

Amabeoku et al. "Evaluation and Application of Digital Rock Physics (DRP) for Special Core Analysis in Carbonate Formations", International Petroleum Technology Conference, Mar. 28, 2013, pp. 26-28, XP055580402.

Saxena et al., "Imaging and Computational Considerations for Image Computed Permeability: Operating Envelope of Digital Rock Physics", Advances in Water Resources, vol. 116, Apr. 4, 2018, pp. 127-144, XP085402086.

Sudakov et al., "Driving Digital Rock Towards Machine Learning: Predicting Permeability With Gradient Boosting and Deep Neural Networks", Mar. 16, 2018, pp. 1-15, XP055678933.

Zecevic et al., "Progress in Electron Tomography to Assess the 3d Nanostructure of Catalysts", Current Opinion in Solid State and Materials Science, vol. 17, 2013, pp. 115-125.

International Search Report and Written Opinion received for PCT Patent Application No. PCT/US2019/066543, mailed on Apr. 1, 2020, 13 Pages.

International Search Report and Written Opinion received for PCT Patent Application No. PCT/US2019/066539, mailed on Apr. 1, 2020, 13 Pages.

International Search Report and Written Opinion received for PCT Patent Application No. PCT/EP2021/067606, mailed on Nov. 17, 2021, 17 pages.

Archie Equation—Aapg Wiki, last modified on Apr. 5, 2022, pp. 1-3, XP055841235.

Dvorkin et al., "Etudes in Computational Rock Physics: Alterations and Benchmarking", Geophysics, vol. 77, Issue No. 3, Jun. 2012, pp. D45-D52.

Fredrich et al., "Digital Rocks: Developing an Emerging Technology Through to a Proven Capability Deployed in the Business", Journal of Petroleum Technology, Oct. 27, 2014, pp. 2383-2399.

International Search Report and Written Opinion received for PCT Patent Application No. PCT/US2021/028299, mailed on Aug. 24, 2021, 12 pages.

Hilpert et al., "Pore-morphology-based Simulation of Drainage in Totally Wetting Porous Media", Advances in Water Resources, Feb.-Mar. 2001, vol. 24, Issue No. 3-4, pp. 243-255.

Alpak et al., "Prediction of Fluid Topology and Relative Permeability in Imbibition in Sandstone Rock by Direct Numerical Simulation", Advances in Water Resources, Dec. 2018, vol. 122, pp. 49-59.

Alpak et al., "Direct Simulation of Pore-scale Two-phase Visco-capillary Flow on Large Digital Rock Images Using a Phase-field

(56) References Cited

OTHER PUBLICATIONS

Lattice Boltzmann Method on General-purpose Graphics Processing Units", Computational Geosciences, Oct. 1, 2019, vol. 23, Issue No. 5, pp. 849-880.

* cited by examiner

METHOD FOR ESTIMATING HYDROCARBON SATURATION OF A ROCK

CROSS REFERENCE TO RELATED APPLICATIONS

This is a National stage application of International application No PCT/US2020/064180, filed Dec. 10, 2020, which claims priority of U.S. application No. 62/947,091, filed 12 Dec. 2019 which is incorporated herein by reference in its entirety.

FIELD OF THE INVENTION

The present invention relates to a method of estimating hydrocarbon saturation of a rock, and, in particular, to a method of estimating hydrocarbon saturation of a rock from a resistivity log and a 3D image of the rock.

BACKGROUND OF THE INVENTION

Accurate determination of hydrocarbon saturation within a hydrocarbon-containing reservoir is an important factor in determining whether to select the hydrocarbon-containing reservoir for development, as well as developing and managing the hydrocarbon-containing reservoir.

Saturation models, like Archie, Waxman-Smits and other electrical conductivity models, are used to calculate the hydrocarbon saturation from a resistivity log. As these equations contain empirical parameters, they must be calibrated against core samples in a laboratory.

One of such empirical parameters is Archie's cementation exponent (often referred to as Archie m). Archie's equation (Archie "Classification of Carbonate Reservoir Rocks and Petrophysical Considerations: AAPG Bulletin 1952; and Archie "The Electrical Resistivity Log as an Aid in Determining Some Reservoir Characteristics" *Transactions of the AIME* 146:54-62; 1942) states that the effective electrical properties of reservoir rocks are fully determined by brine conductivity, the sample's total porosity and the connectivity of the pore space. The cementation exponent is typically determined by physical testing of rock samples using laboratory measurements of effective electrical conductivity of the rock, total porosity of the rock, and conductivity of the brine fully saturating pores of the rock.

Such tests, however, require substantial time and are quite expensive. Further, the number of samples that may be processed is relatively limited due to the time and expense required to conduct each test. There is a need for providing information more quickly in order to make more timely decisions.

Digital rock physics is a technology that has been developed to provide faster, more, and less expensive analysis of hydrocarbon-containing formation rocks to determine key petrophysical characteristics of the rocks. Digital rock physics utilizes digital images of formation rocks to simulate rock multiphysics at the pore scale and to predict properties of complex rocks.

For example, U.S. Pat. No. 8,311,788B2 (Hurley et al) describes a method for quantifying pore shapes, volumes and surface areas using confocal profilometry.

U.S. Pat. No. 10,466,386B2 (Hurley) discloses methods for determining a saturation-height function in oil and gas reservoirs. The saturation-height function is determined by analyzing core samples to quantify absolute values of microporosity and calculating based on distribution of facies and microporosity that is determined as a function of height based on the absolute values. A correlation is established between the microporosity and facies. Absolute values of microporosity are determined using laser scanning confocal microscopy and/or mercury injection capillary pressure (MICP). A microporosity-weighted water saturation is determined using an Archie (n) value, determined by computing from digital models based on 3D confocal scans, to combine a water saturation value with a pore-network value and a borehole-image facies.

U.S. Pat. No. 9,134,457B2 (Hurley et al) relates to multiscale rock modeling for reservoir simulation. According to Hurley '457, pore-scale (nm to μm) digital rock modeling data is upscaled to borehole-scale (mm to m) digital rock modeling data, which is then upscaled to inter-well-scale (10's to 100's of m), which, in turn, is then upscaled to full-field-scale (10's of km) digital rock modeling data. The pore-scale digital rock modeling data includes pore geometry that is quantified by transmitted laser scanning fluorescence microscopy, micro-CT scans, nano-CT scans, focused ion beam-scanning electron microscopy, MICP, and/or nuclear magnetic resonance, using core plugs selected from gridded permeability and conventional CT scan data of core slabs. The full-field-scale digital rock modeling data is based on interwell-scale computed values, such as porosities, permeabilities, capillary pressures, resistivity indices, relative permeabilities, water saturations, irreducible water saturations, residual oil saturations, recovery factors, and Archie cementation (m) and saturation (n) exponents.

Digital Rock Physics can lead to rapid acceleration of results for upstream exploration and development projects and offers the possibility of simulating rock properties using properties of field crude and brine, as well as any digital alterations to mineral conductivity. The computed effective conductivity of a digital rock directly depends on the fraction of conductive pore space that is accessible to the simulator.

Digital rock physics modelling conventionally has relied on an assumption that the pore volume of hydrocarbon-containing rocks is accurately determined from micron-scale images. However, micron-scale X-ray computer tomography images, generated by current imaging technology, are limited in resolution and thus a significant portion of rock pore volume can remain unresolved. The missing pore volume is not accessible to direct numerical solvers that are used to compute effective electrical conductivity to effectively estimate Archie's cementation exponent. This limits applicability of Digital Rock technology.

For example, as discussed in Saxena et al, 2019 ("Estimating Pore Volume of Rocks from Pore-Scale Imaging" Transport in Porous Media 129: 403-412; 2019), due to current resolution limit of micron-scale images generated by micro-CT detectors, up to half of the total pore volume can be missing in micro-CT images of reservoir rocks.

There is a need for correctly parameterizing saturation models to include the impact of sub-resolution pore volume on effective conductivity so that the associated empirical constants, such as the cementation exponent, can be estimated accurately.

SUMMARY OF THE INVENTION

According to one aspect of the present invention, there is provided a method for estimating hydrocarbon saturation of a hydrocarbon-bearing rock from a resistivity log and a rock image, comprising: obtaining a resistivity log for a field having a hydrocarbon-bearing formation; obtaining a 3D image of a rock from the hydrocarbon-bearing formation in the field, wherein the 3D image is comprised of a plurality of voxels and the 3D image has a resolution; processing the 3D image to segment the 3D image by selecting each voxel of the 3D image to represent either a pore space in the rock or solid material in the rock; estimating an image porosity of the rock from the segmented 3D image, the image porosity lacking a sub-resolution porosity of the rock; determining a corrected porosity adapted to account for the sub-resolution porosity of the rock; estimating a corrected cementation exponent of the rock from the image porosity and the corrected porosity of the rock; and estimating the hydrocarbon saturation of the hydrocarbon-bearing rock using the corrected cementation exponent.

According to another aspect of the present invention, there is provided a backpropagation-enabled method for estimating a hydrocarbon saturation of a hydrocarbon-bearing rock, comprising the steps of: obtaining a resistivity log for a field having a hydrocarbon-bearing formation; obtaining a 3D image of a rock from the hydrocarbon-bearing formation in the field, the 3D image having a resolution; applying a backpropagation-enabled trained model to segment the 3D image; estimating an image porosity of the rock from the segmented 3D image, the image porosity lacking a sub-resolution porosity of the rock; determining a corrected porosity adapted to account for the sub-resolution porosity of the rock; estimating a corrected cementation exponent of the rock from the image porosity and the corrected porosity of the rock; and estimating the hydrocarbon saturation of the hydrocarbon-bearing rock using the corrected cementation exponent.

According to a further aspect of the present invention, there is provided a backpropagation-enabled method for estimating the hydrocarbon saturation of rock from an image of rock, comprising the steps of: obtaining a resistivity log for a field having a hydrocarbon-bearing formation; obtaining an image of rock from the hydrocarbon-bearing formation in the field, the image selected from the group consisting of a series of 2D projection images, 3D reconstructed images and combinations thereof; and applying a backpropagation-enabled trained model to obtain a hydrocarbon saturation of the rock.

BRIEF DESCRIPTION OF THE DRAWINGS

The present invention will be better understood by referring to the following detailed description of preferred embodiments and the drawings referenced therein, in which.

DETAILED DESCRIPTION OF THE INVENTION

Figure 1:
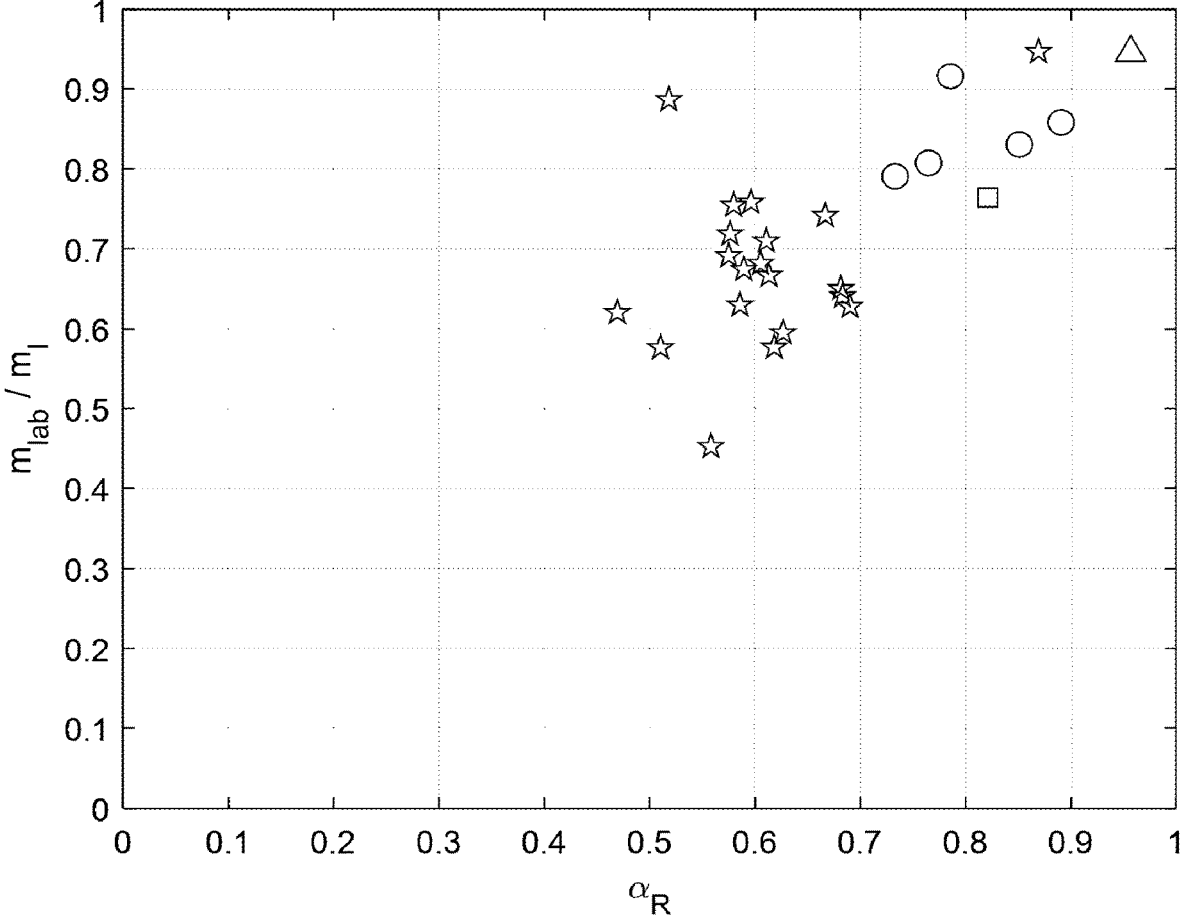
FIG. 1 is a graphical illustration comparing laboratory-measured values of Archie m with corresponding values of Archie m determined from 3D images the rock.

In accordance with the method of the present invention, hydrocarbon saturation of a rock can be estimated more quickly from 3D images than conducting laboratory measurements. Specifically, the method of present invention estimates hydrocarbon saturation based on a cementation exponent, specifically Archie m, derived from direct simulations. More specifically, a meaningful estimate of the cementation exponent is determined by correcting an image-derived cementation exponent determined from micron-scale images. In a preferred embodiment, the image-derived cementation exponent is corrected for sub-resolution pore volume missing from lower resolution images.

The present inventors have surprisingly discovered that capillary physics in rocks can be used to quantify the impact of image resolution on porosity. This discovery enables Digital Rock or Digital Rock Physics to provide capability to determine a cementation exponent from 3D images of rocks generated by micro-CT technology. The inventors have discovered a method to estimate a corrected cementation exponent. Advantageously, the corrected cementation exponent, and therefore hydrocarbon saturation, compensates for the limited image resolution without the need for higher resolution imaging that is only possible at the expense of image field of view or physical laboratory measurement.

The present invention provides a method for more accurately estimating hydrocarbon saturation of a rock based on an original 3D pore-scale image of the rock having limited resolution relative to the actual pore structure of the rock. Contrary to current assumptions in digital rock physics modelling, the inventors recognized that a substantial fraction of the pore volume of hydrocarbon-containing rocks is contained in pores of a size below the image resolution provided by 3D pore-scale imaging technology commonly used to provide images of such rocks. As a result, conventional digital rock physics modelling substantially underpredicts the effective electrical conductivity of the rock by failing to account for pores that are smaller than the image resolution of the pore-scale imaging technology in the cementation exponent, and therefore the hydrocarbon saturation, computation.

The present invention also provides a backpropagation-enabled method for estimating the hydrocarbon saturation of rock from a 3D image of rock. A backpropagation-enabled trained model is applied to a 3D image to segment the 3D image of rock.

In a preferred embodiment, the trained model is produced by providing a training set of images of rock, segmenting the images into a plurality of labeled voxels, the plurality of labeled voxels representing pore spaces and solid material in the rock, and using the labeled voxels to train a model via backpropagation.

The training set of images of rock may include, for example, 2D projection images obtained from a pore-scale imaging technology, 3D images reconstructed from 2D projection images, synthetic 2D images, synthetic 3D images, and combinations thereof. In a preferred embodiment, the training set of images is obtained from a cloud-based tool adapted to store 2D projection images from a pore-space imaging technology, especially micro-CT and thin sections. The tool is adapted to process the 2D projection images to produce a reconstructed 3D image. The tool is also adapted to store the resulting 3D images.

Examples of backpropagation-enabled processes include, without limitation, artificial intelligence, machine learning, and deep learning. It will be understood by those skilled in the art that advances in backpropagation-enabled processes continue rapidly. The method of the present invention is expected to be applicable to those advances even if under a different name. Accordingly, the method of the present invention is applicable to the further advances in backpropagation-enabled processes, even if not expressly named herein.

A preferred embodiment of a backpropagation-enabled process is a deep learning process, including, but not limited to a convolutional neural network.

The backpropagation-enabled process may be supervised, semi-supervised, unsupervised or a combination thereof. In one embodiment, a supervised process is made semi-supervised by the addition of an unsupervised technique.

In a supervised backpropagation-enabled process, the training set of images is labeled to provide examples of pore spaces and solid material of interest. In an unsupervised backpropagation-enabled process, a pore space and/or solid material of interest may be identified by, for example, drawing a polygon around the image of interest in the image. The trained process will then identify areas of interest having similar latent space characteristics. When the training set is labeled images, the labels may have a dimension of 1D-3D.

In one embodiment, the supervised backpropagation-enabled process is a classification process. The classification process may be conducted voxel-wise, slice-wise and/or volume-wise.

In another embodiment, the unsupervised backpropagation-enabled process is a clustering process. The clustering process may be conducted voxel-wise, slice-wise and/or volume-wise.

In another embodiment, the unsupervised backpropagation-enabled process is a generative process. The generative process may be conducted voxel-wise, slice-wise and/or volume-wise.

Preferably, the backpropagation-enabled process is a segmentation process.

In a preferred embodiment, the training step includes validation and testing.

In the method of the present invention, petrophysical characteristics of a rock, particularly the hydrocarbon saturation of the rock, may be estimated from a well resistivity log and an image of the rock. A resistivity log is obtained for a field having a hydrocarbon-bearing formation. The resistivity log is obtained in a conventional manner and form known to those skilled in the art. The rock image is obtained from a rock from the hydrocarbon-containing formation for which the petrophysical characteristics of the formation, or portion thereof, are of interest. Preferably, the rock may be a sandstone, a carbonate, a shale and combinations thereof from a hydrocarbon-containing formation. The rock may be obtained by conventional means for obtaining rock samples from a hydrocarbon formation. In a preferred embodiment, a core sample of the rock is obtained by coring a portion of the formation from within a well in the formation. Alternatively, a sample of the rock may be obtained from drill cuttings produced in drilling a well in the formation. The rock may be obtained from the same wellbore as the resistivity log. Alternatively, the rock may be obtained from another wellbore in the same field as the wellbore for which the resistivity log was produced.

The rock sample should be of sufficient size to obtain a 3D image of sufficient volume at the scale that the image is generated. In particular, the rock sample should be of sufficient size such that characteristics of the bulk of the sample predominate over the characteristics of the edges of the sample at the scale or field of view of the image to be generated.

A 3D image comprised of a plurality of voxels is obtained from the rock sample. The 3D image of the rock may be obtained utilizing pore-scale imaging technology. A 3D image of the rock may be obtained by x-ray computer tomography, including, without limitation, x-ray micro-computed tomography (micro-CT) and x-ray nano-computed tomography (nano-CT), acoustic microscopy, or magnetic resonance imaging. Most preferably, the 3D image of the rock is obtained by micro-CT to provide sufficient field of view of the rock to avoid edge pores distorting the overall porosity of the resulting image, as well as to reduce scanning time and computational requirements that higher resolution tomography (e.g. nano-CT) would require.

In a preferred embodiment, the 3D image is obtained from a cloud-based tool adapted to store 2D projection images from a pore-space imaging technology, especially micro-CT and thin sections. The tool is adapted to process the 2D projection images to produce a reconstructed 3D image. The tool is also adapted to store the resulting 3D images.

The 3D image of the rock obtained by pore-scale imaging technology has a resolution. The voxels of the 3D image define the resolution of the image. The image is comprised of a plurality of voxels, where the volume defined by each voxel represents a maximum resolution of the image. The resolution of the image should be selected to provide a voxel size at which the dominant pore throats for fluid flow in the rock are sufficiently resolved and at which a sufficient field of view is provided so as to be representative of the whole rock for a given petrophysical property to be analyzed (e.g. cementation exponent and hydrocarbon saturation). For purposes herein, the dominant pore throat size ($D_d$) is the size of pore throats of pores that a non-wetting liquid enters at the pore entry pressure ($P_d$), where the pore entry pressure is the minimum pressure required before the non-wetting liquid can begin to invade the pore structure of the rock.

The resolution of a micro-CT image may be chosen based on the size of the rock sample, the relative average pore size of the type of rock, the time required for the imaging, and the computational power required to store and conduct further computational activity on the image data. The image resolution is chosen to be detailed enough that a non-wetting liquid capillary injection curve can be plotted based on a segmented image produced from the image while maintaining a sufficient field of view to avoid edge pores distorting the overall porosity of the resulting image. In a preferred embodiment, the image resolution is selected to require as little computational power to store and conduct further computational activity on the image while providing sufficient detail to construct a capillary injection curve based on the segmented image. The image resolution may be selected based on the type of rock, where sandstones generally have a larger pore structure than carbonates, and require less image resolution than carbonates, and carbonates have a larger pore structure than shales, and require less image resolution than shales. The resolution of the micro-CT image may range from 0.1 $\mu m^3$ to 30 $\mu m^3$ per voxel. For sandstones, the micro-CT image preferably is produced at a resolution of from 1 $\mu m^3$ to 25 $\mu m^3$ per voxel, or from 2.5 $\mu m^3$ to 15 $\mu m^3$ per voxel; for carbonates the resolution of the micro-CT image may range from 0.5 $\mu m^3$ to 20 $\mu m^3$, or from 1 $\mu m^3$ to 10 $\mu m^3$; and for shales the resolution of the micro-CT (or nano-CT) image may range from 0.1 $\mu m^3$ to 10 $\mu m^3$, or from 0.5 $\mu m^3$ to 5 $\mu m^3$.

In a preferred embodiment, the acquired image may be processed to reduce noise and image artifacts. Noise may be filtered from the acquired image by filtering using a local means filter to reduce noise. Imaging artifacts, predominant at the outer edges of the acquired image, may be reduced by processing the image while excluding the outer edges of the image.

The 3D image obtained for the rock is processed to segment the voxels of the image into voxels representing either pore space in the rock or solid material in the rock, thereby producing a binary image in which pore voxels have a value of 0 and solid material voxels have a value of 1 (or vice versa). The image may be a grayscale image, and processing the voxels of the image to segment the image into voxels representing pore space or solid material may be effected by assigning a voxel a designation as pore space or as solid material based on a threshold, wherein voxels having an image intensity above the threshold may be assigned a value representing a pore (or solid material) and voxels having an image intensity below the threshold may be assigned a value representing solid material (or a pore). A threshold may be calculated using Otsu's method as described in Otsu ("A Threshold Selection Method from Gray-level Histogram" *IEEE Trans. SMC* 9:62-66; 1979), or other threshold calculation algorithms known in the art.

The 3D image of the rock may be processed to segment the voxels into pore space voxels and solid material voxels utilizing segmentation algorithms known in the art. Preferably, the segmentation method is selected to differentiate conductive pores from non-conductive minerals. Examples of segmentation methods are described in Otsu (1979), Andra et al ("Digital Rock Physics Benchmarks-Part II: Computing Effective Properties" *Computers and Geosciences* 50:33-43; 2013), Saxena et al ("Effect of Image Segmentation & Voxel Size on Micro-CT Computed Effective Transport & Elastic Properties" *Marine and Petroleum Geology* 86:972-990; 2019), and Chuang et al ("Fuzzy C-Means Clustering with Spatial Information for Image Segmentation" *Comput. Med. Imaging Graph.* 30:9-15; 2006). The desired selection of segmentation will be understood by those skilled in the art. Segmentation using segmentation algorithms is preferably conducted automatically using data processing systems.

After the image has been segmented, an image porosity, $\phi_I$, is estimated from the segmented 3D image of the rock. The image porosity of the rock may be estimated by summing the number of voxels in the segmented image that represent pore space, summing the total number of voxels in the segmented image (or obtaining the total number of voxels from the imaging parameters), then dividing the sum of the number of voxels in the segmented image that represent pore space by the total number of voxels in the segmented image. A sum of the number of voxels in the segmented image that represent pore space may be determined by adding up the number of voxels assigned a binary value (e.g. 1 or 0) representing pore space. A sum of the total number of voxels in the segmented image may be determined by adding up the total number of voxels assigned a binary value, both pore space voxels and solid material voxels. The image porosity lacks a sub-resolution porosity of the rock.

In accordance with the present invention, a corrected porosity adapted to account for the sub-resolution porosity of the rock is determined. In one embodiment of the present invention, a corrected porosity is measured using a conventional laboratory measurement. In another embodiment of the present invention, a corrected porosity is determined by applying a correction factor to the image porosity, for example by a relation between the image porosity ($\phi_I$), true porosity ($\phi_\infty$), and a correction factor ($\alpha$) may be expressed as follows:

$$\phi_I = \alpha \phi_\infty \text{ where } 0 < \alpha < 1. \tag{1}$$

The correction factor may be estimated by a transform. In a preferred embodiment, the correction factor is determined by determining a non-wetting liquid capillary pressure curve from the segmented 3D image of the rock for pores distinguishable in the segmented image at pressures up to an image-limited pressure. Preferably mercury or Wood's metal is selected as the non-wetting liquid. A non-wetting liquid capillary pressure curve may be determined from the segmented image by plotting the porosity of the rock occupied by the non-wetting liquid at selected pressures up to the image-limiting pressure based upon simulations of the non-wetting liquid filling the pore space of the image. To simulate the non-wetting liquid filling the pore space of the image, the pore throat size penetrated at a given pressure may be determined according to the Young-Laplace equation:

$$D = 4\sigma \cos \theta / P \tag{2}$$

where P is the given pressure, $\sigma$ is the non-wetting liquid-air surface tension (480 dyne/cm for mercury-air), $\theta$ is the contact angle (140° for mercury) and D is the pore throat size penetrated at the given pressure. To evaluate the porosity of the rock occupied by a non-wetting liquid at a given pressure, a simulation may be conducted in which voxels of pore space of pore bodies having a pore throat size of D or larger are assumed to be filled with the non-wetting liquid at the given pressure, the voxels that are "filled" with the liquid are summed, and the porosity of the rock occupied by the non-wetting liquid is calculated by dividing the sum of the number of pore space voxels filled with liquid by the total number of voxels in the image. The porosity of the rock occupied by the non-wetting liquid may then plotted against the given pressure for a number of selected given pressures above the entry pressure ($P_d$) up to the image-limited pressure ($P_{max}$). The entry pressure ($P_d$) is the pressure at which the non-wetting liquid initially enters pores in the rock, and the image-limited pressure ($P_{max}$) is the minimum pressure required to overcome the capillary pressure of the narrowest pore throat distinguishable in the segmented image.

Thomeer's model of the Capillary Pressure Curve provides that:

$$\varphi_P = \varphi_\infty (e^{-G/Log10(N)}) \tag{3}$$

where $\varphi_P$ is the porosity of the rock occupied by a non-wetting liquid at pressure P, $\varphi_\infty$ is the porosity of the rock occupied by a non-wetting liquid at infinite pressure (the true porosity since the pressure is sufficient to force the non-wetting liquid through the smallest pore throat in the rock), G is the pore geometric factor reflecting the distribution of pore throats and their associated pore bodies' volume, and N is the pore throat resolution parameter. When P is equal to the image-limiting pressure, then $$\varphi_I = \varphi_\infty (e^{-G/Log10(N)}) \tag{4}$$

and the porosity correction factor $\alpha_R = (e^{-G/Log10(N)})$. The porosity correction factor $\alpha_R$, therefore, can be determined from the pore geometric factor G and the pore resolution parameter N.

The pore resolution parameter N is determined from the non-wetting liquid capillary pressure curve derived from the image and the image resolution as determined from the size of the voxels. The pore resolution parameter N is the ratio of the pore throat size ($D_d$) entered by the non-wetting liquid at the entry pressure ($P_d$) to the size of the voxels ($\Delta x$), $N = (D_d / \Delta x)$. The size of the voxels may be determined from the parameters of the 3D imaging (i.e. the resolution of the image). The pore throat size ($D_d$) of pores entered by the non-wetting liquid at entry pressure ($P_d$) may be determined from the non-wetting liquid capillary pressure curve derived from the segmented 3D image of the rock according to the equation:

$$D_d = 4\sigma \cos \theta / P_d \tag{5}.$$

The pore geometric factor G is determined from the non-wetting liquid capillary pressure curve derived from the image. The pore geometric factor G may be determined by plotting a best fit curve to the non-wetting liquid capillary pressure curve simulated from the segmented image and determining the pore geometric factor from the shape of the curve. The best fit curve may be plotted by the least squares method or by any conventional curve-fitting method.

As described above, the pore geometric factor G and the pore throat resolution parameter N are utilized to determine the porosity correction factor. The porosity correction factor α may be calculated from the pore geometric factor G and the pore throat resolution parameter N according to the equation:

$$\alpha_R = (e^{-G/Log10(N)}) \tag{6}$$

The porosity correction factor $\alpha_R$ is then applied to the image porosity of the rock to obtain a corrected porosity. The corrected porosity ($\varphi_\infty$) may be estimated from the image porosity ($\varphi_I$) of the rock and the porosity correction factor ($\alpha$) according to the following equation:

$$\varphi_I / \alpha = \varphi_\infty \tag{7}$$

The corrected porosity is substantially the same as the true porosity determined with laboratory measurements.

As mentioned above, Archie's equation (Archie, 1942, 1952) states that the effective electrical properties of reservoir rocks are fully determined by brine conductivity, the sample's total porosity and the connectivity of the pore space:

$$\frac{1}{FF_\infty} = \frac{C_{0\infty}}{C_w} = \phi_\infty^{m_\infty} \tag{8}$$

where $C_w$ is conductivity of brine that completely saturates all pores, $\phi_\infty$ is total porosity of the rock, $C_{0\infty}$ is the effective conductivity of brine saturated rock, $FF_\infty$ is the so-called formation factor, and is the cementation exponent. The symbol ∞ indicates properties computed using a hypothetical image of very high resolution such that the entire pore volume is resolved. Properties computed for very high-resolution (denoted by ∞) are comparable with laboratory measurements.

However, for rock images at a finite voxel size, such as micro-CT, the inventors' Archie's equation is rewritten as $$\frac{1}{FF_I} = \frac{C_{0I}}{C_w} = \phi_I^{m_I}, \tag{9}$$

where the subscript "I" refers to properties computed using a segmented image separated into conductive pores and non-conductive minerals.

Equation (9) represents the inventors' recognition that image-derived properties, especially for lower resolution images, do not match those measured in the laboratory. The inventors recognized that, without correcting for missing sub-resolution porosity, because $\phi_I < \phi_\infty$, the computed effective electrical conductivity of the rock using the segmented micro-CT image is underpredicted (i.e., $C_{0I} < C_{0\infty}$, and $FF_I > FF_\infty$).

Accordingly, the method of the present invention compensates for the sub-resolution pore volume by modifying the Archie equation that can be solved to estimate the cementation exponent $m_\infty$ using image-derived properties:

$$\frac{1}{FF_\infty} = \frac{C_{0I}}{C_w} + (\phi_\infty - \phi_I)^k = \phi_\infty^{m_\infty}, \tag{10}$$

or $$\frac{1}{FF_\infty} = \frac{C_{0I}}{C_w} + (\phi_I/\alpha_R - \phi_I)^k = (\phi_I/\alpha_R)^{m_\infty}. \tag{11}$$

The term $(\phi_\infty - \phi_I)^k$ in Equation (10) is a normalized conductivity correction term that compensates for the under-prediction of effective electrical conductivity of the rock due to missing sub-resolution porosity in the micro-CT image.

The inventors have discovered that the exponent k has a near linear relation with $\alpha_R$ with the following empirical relations:

$$k = (k_0 - m_\infty)\alpha_R + m_\infty, \text{ where } k_0 = 0.9 \tag{12}$$

$$\frac{C_{0I}}{C_w} + (\phi_I/\alpha_R - \phi_I)^{(k_0 - m_\infty)\alpha_R + m_\infty} = (\phi_I/\alpha_R)^{m_\infty} \tag{13}$$

$$m_\infty < \frac{\alpha_R k_0}{\alpha_R - 1 + \frac{\log(\phi_I/\alpha_R)}{\log(\phi_I/\alpha_R - \phi_I)}} \tag{14}$$

According to one embodiment of the present invention, an image Archie cementation exponent ($m_I$) is corrected for the missing pore volume contained in pores smaller than the image voxel size. As discussed in Saxena et al 2019, parameter $\alpha_R$ can be estimated directly from images without using any laboratory measurements other than a single micro-CT image for homogenous rock samples. Therefore, all parameters required to estimate $m_\infty$ using Equation (13) can be estimated directly using a micro-CT image. The remaining parameters that need to be estimated using a micro-CT image are: the porosity of the segmented micro-CT image ($\phi_I$), brine conductivity ($C_w$) which is an input into the numerical simulation, and the effective electrical conductivity of segmented micro-CT image ($C_{0I}$).

The effective electrical conductivity of a rock sample depends on the conductivities of the constituents, including minerals and the pore-filling fluids. In the static direct current limit, the electrical current density field is described by the diffusion equation for the electrical potential. As an example, all solid grains, including any clays, can be assumed to be perfectly insulating, and therefore the conductivity can be assigned values of 0 in the solid matrix and a finite fluid conductivity in the pore fluid. The effective conductivity is then obtained using Ohm's law relating the total electrical current and the voltage between the inlet and the outlet boundaries. One method is described in Garboczi ("Finite element and finite difference programs for computing the linear electric and linear elastic properties of digital images of random materials" NISTIR 6269; 1998).

Hydrocarbon saturation can then be estimated by calculating water saturation. Archie's equation is expressed as follows:

$$S_w^n = \frac{R_w}{(\phi^m \times R_t)} \tag{15}$$

where $S_w$ is water saturation of an uninvaded zone, n is a saturation exponent (Archie n), $R_w$ is the formation water resistivity, $\phi$ is porosity, m is the cementation exponent (Archie m), and $R_t$ is the true resistivity of the formation, corrected for invasion, borehole, thin bed and other effects. Hydrocarbon saturation is 1 minus the water saturation value.

The $R_W$ can be determined by log or physical measurement methods known to those skilled in the art. Archie n can be determined by conventional lab measurement or by estimating according to Archie's guidance (for example, as discussed at https://wiki.aapg.org/Archie_equation).

Preferably, the estimated hydrocarbon saturation is used to convert the resistivity log to a continuous saturation profile, in a manner known to those skilled in the art, for example, using a density log for the field from which the resistivity log was obtained. More accurate estimations of hydrocarbon saturation, as well as continuous saturation profiles derived therefrom, are particularly suitable for exploration and production decisions, and field appraisals. The method of the present invention enables quick decision-making. For example, a process for estimating hydrocarbon saturation using physical measurements of a rock sample may take in the order of 7 to 8 months, while the method of the present invention can provide substantially the same or better accuracy in a matter of days.

EXAMPLE

The following non-limiting example of an embodiment of the method of the present invention as claimed herein is provided for illustrative purposes only.

True cementation exponents were determined in a physical laboratory using laboratory measured electrical conductivity of the rock, laboratory measured porosity, and conductivity of brine saturating pores of different rock types from Gulf of Mexico and Brunei. The true cementation exponent, $m_{lab}$ was calculated from Equation (8). Cementation exponents were derived from 3D micro-CT images for the same rock samples. The image-derived cementation exponents, $m_I$, were calculated from Equation (9). The $m_{lab}/m_I$ ratio is illustrated in FIG. 1 against $\alpha_R$. FIG. 1 shows that, as $\alpha_R$ approaches 1, there is good agreement between the lab-measured and image-derived cementation exponents. But, for example, when $\alpha_R=0.5$, there is deviation between the lab-measured and image-derived cementation exponents.

Figure 2:
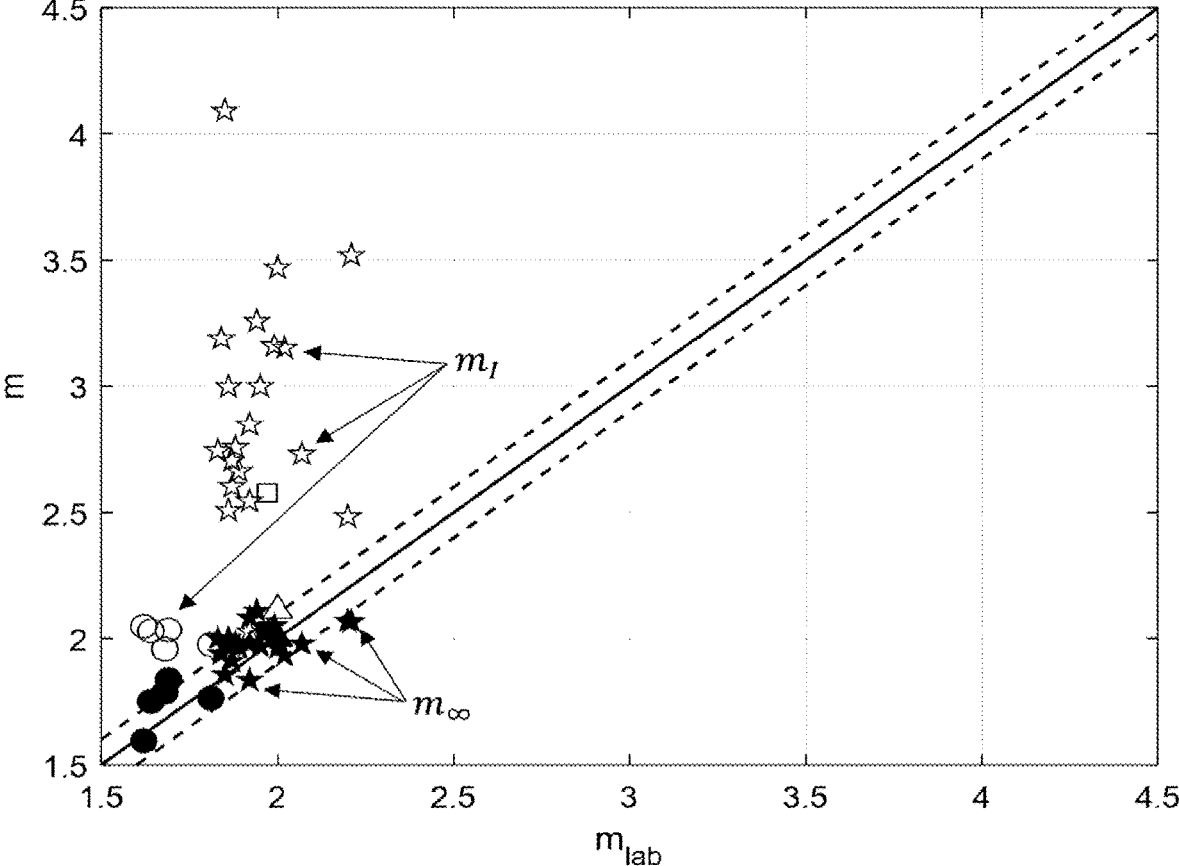
FIG. 2 is a graphical illustration comparing laboratory-measured values of Archie m with corresponding corrected values of Archie m.

FIG. 2 illustrates laboratory measured cementation exponents, $m_{lab}$, compared with those estimated using micro-CT images before $(m_I)$ and after transform $(m_\infty)$ using Equation (13). FIG. 2 illustrates that $m_I$ is overestimated without correction in accordance with the method of the present invention.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method for estimating hydrocarbon saturation of a hydrocarbon-bearing rock from a resistivity log and a rock image, comprising:

obtaining a resistivity log and a density log for a field having a hydrocarbon-bearing formation;

obtaining a 3D image of a rock from the hydrocarbon-bearing formation in the field, wherein the 3D image is comprised of a plurality of voxels and the 3D image has a resolution;

processing the 3D image to segment the 3D image by selecting each voxel of the 3D image to represent either a pore space in the rock or solid material in the rock;

estimating an image porosity of the rock from the segmented 3D image, the image porosity lacking a sub-resolution porosity of the rock;

determining a corrected porosity adapted to account for the sub-resolution porosity of the rock;

estimating a corrected cementation exponent of the rock from the image porosity and the corrected porosity of the rock;

estimating the hydrocarbon saturation of the hydrocarbon-bearing rock using the corrected cementation exponent; and converting the resistivity log to a continuous saturation profile using the estimated hydrocarbon saturation and the density log.

2. The method of claim 1, wherein the 3D image of the rock is obtained by x-ray computer tomography.

3. The method of claim 1, wherein the step of estimating the hydrocarbon saturation comprises determining a formation water resistivity and a saturation exponent.

4. The method of claim 1, wherein the rock is obtained from a hydrocarbon-bearing formation comprised of sandstone, carbonate, shale and combinations thereof.

5. The method of claim 1, wherein the corrected porosity of the rock is determined by laboratory measurement.

6. The method of claim 1, wherein the corrected porosity of the rock is determined by deriving a non-wetting liquid capillary pressure curve from the segmented 3D image of the rock; and determining the corrected porosity from the segmented 3D image and the non-wetting liquid capillary pressure curve.

7. The method of claim 6, wherein the non-wetting liquid capillary pressure curve is derived from the segmented 3D image of the rock at pressures of up to an image-limited pressure, where the image-limited pressure is the minimum pressure that can be applied on the non-wetting liquid to overcome the capillary pressure of the narrowest pore throat distinguishable from the segmented 3D image of the rock.

8. The method of claim 1, wherein the 3D image is obtained from a cloud-based tool adapted to store and process 2D projection images from a pore-scale imaging technology.

5

\* \* \* \* \*